(12) United States Patent
Brannan

(10) Patent No.: US 8,343,145 B2
(45) Date of Patent: Jan. 1, 2013

(54) MICROWAVE SURFACE ABLATION USING CONICAL PROBE

(75) Inventor: Joseph D. Brannan, Erie, CO (US)

(73) Assignee: Vivant Medical, Inc., Boulder, CO (US)

( * ) Notice: Subject to any disclaimer, the term of this patent is extended or adjusted under 35 U.S.C. 154(b) by 624 days.

(21) Appl. No.: 12/568,551

(22) Filed: Sep. 28, 2009

(65) Prior Publication Data
US 2011/0077634 A1  Mar. 31, 2011

(51) Int. Cl.
*A61B 18/18* (2006.01)

(52) U.S. Cl. ............... 606/33; 606/22; 606/41; 607/156

(58) Field of Classification Search ............... 607/154, 607/156, 115, 116; 606/22, 33, 41
See application file for complete search history.

(56) References Cited

U.S. PATENT DOCUMENTS

| | | | |
|---|---|---|---|
| 4,752,141 A | 6/1988 | Sun et al. | |
| 4,823,812 A * | 4/1989 | Eshel et al. | ........... 607/156 |
| 4,883,354 A | 11/1989 | Sun et al. | |
| 4,988,212 A | 1/1991 | Sun et al. | |
| 5,029,588 A | 7/1991 | Yock et al. | |
| 5,944,749 A | 8/1999 | Fenn | |
| 6,026,331 A | 2/2000 | Feldberg et al. | |
| 6,036,698 A | 3/2000 | Fawzi et al. | |
| 6,136,014 A | 10/2000 | Sirimanne et al. | |
| 6,287,302 B1 | 9/2001 | Berube | |
| 6,306,132 B1 | 10/2001 | Moorman | |
| 6,355,033 B1 | 3/2002 | Moorman | |
| 6,405,733 B1 | 6/2002 | Fogarty et al. | |
| 6,471,696 B1 | 10/2002 | Berube et al. | |
| 6,471,709 B1 | 10/2002 | Fawzi et al. | |
| 6,527,768 B2 | 3/2003 | Berube | |
| 6,564,806 B1 | 5/2003 | Fogarty et al. | |
| 6,582,426 B2 | 6/2003 | Moorman | |
| 6,652,520 B2 | 11/2003 | Moorman | |
| 6,722,371 B1 | 4/2004 | Fogarty et al. | |
| 6,752,154 B2 | 6/2004 | Fogarty et al. | |

(Continued)

FOREIGN PATENT DOCUMENTS
DE  390937  3/1924
(Continued)

OTHER PUBLICATIONS
U.S. Appl. No. 09/195,118, filed Nov. 18, 1998.
(Continued)

*Primary Examiner* — Linda Dvorak
*Assistant Examiner* — Jocelyn D Ram

(57) ABSTRACT

An electromagnetic surgical ablation probe having a conical hood reflector and method of manufacture thereof is disclosed. The disclosed probe includes a shaft assembly that has a coaxial feedline core having an inner conductor and an outer conductor separated by an insulating layer. A tubular catheter is disposed coaxially around the feedline and is configured to deliver coolant, such as saline or deionized water, to a coolant chamber at a distal end formed within the conical reflector. A radiating section disposed within the conical reflector may have a conical, cylindrical, or other suitable shape. A membrane disposed across a distal opening of the conical reflector seals coolant within the coolant chamber, and may conform to tissue contours during use. A resilient aperture may be included at the periphery of the conical hood. The shaft assembly may include an angled section, an adjustable section, and, additionally or alternatively, a malleable section.

3 Claims, 14 Drawing Sheets

U.S. PATENT DOCUMENTS

| | | |
|---|---|---|
| 6,752,767 B2 | 6/2004 | Prakash |
| 6,878,147 B2 | 4/2005 | Prakash |
| 7,128,739 B2 | 10/2006 | Prakash et al. |
| 7,147,632 B2 | 12/2006 | Prakash et al. |
| 7,160,292 B2 | 1/2007 | Moorman et al. |
| 7,197,363 B2 | 3/2007 | Prakash et al. |
| 7,318,824 B2 | 1/2008 | Prakash et al. |
| 7,326,201 B2 | 2/2008 | Fjield et al. |
| 7,393,352 B2 | 7/2008 | Berube |
| 7,468,042 B2 | 12/2008 | Turovskiy |
| 7,527,623 B2 | 5/2009 | Prakash et al. |
| 7,594,313 B2 | 9/2009 | Prakash et al. |
| 7,642,451 B2 | 1/2010 | Bonn |
| 7,645,142 B2 | 1/2010 | McMunigal et al. |
| 2001/0029368 A1* | 10/2001 | Berube ............ 606/33 |
| 2003/0060813 A1 | 3/2003 | Loeb |
| 2005/0038419 A9 | 2/2005 | Arnold et al. |
| 2006/0259024 A1 | 11/2006 | Turovskiy et al. |
| 2006/0264923 A1 | 11/2006 | Prakash et al. |
| 2006/0282069 A1 | 12/2006 | Prakash et al. |
| 2006/0293650 A1 | 12/2006 | Prakash et al. |
| 2007/0161977 A1 | 7/2007 | Moorman et al. |
| 2007/0198006 A1 | 8/2007 | Prakash et al. |
| 2008/0082093 A1 | 4/2008 | Prakash et al. |
| 2008/0135217 A1 | 6/2008 | Turovskiy et al. |
| 2008/0266203 A1 | 10/2008 | Rosetto et al. |
| 2008/0275438 A1 | 11/2008 | Gadsby et al. |
| 2008/0294162 A1 | 11/2008 | Rosetto et al. |
| 2008/0308256 A1 | 12/2008 | Deborski et al. |
| 2008/0319434 A1 | 12/2008 | Rick et al. |
| 2009/0005766 A1 | 1/2009 | Brannan |
| 2009/0018536 A1 | 1/2009 | Behnke |
| 2009/0030412 A1* | 1/2009 | Willis et al. ............ 606/41 |
| 2009/0036883 A1 | 2/2009 | Behnke |
| 2009/0076492 A1 | 3/2009 | Behnke |
| 2009/0084581 A1 | 4/2009 | Johnson et al. |
| 2009/0130897 A1 | 5/2009 | McMunigal et al. |
| 2009/0131926 A1 | 5/2009 | Rusin et al. |
| 2009/0137145 A1 | 5/2009 | Arts et al. |
| 2009/0138004 A1 | 5/2009 | Bonn |
| 2009/0149850 A1 | 6/2009 | Turovskiy et al. |
| 2009/0187180 A1 | 7/2009 | Brannan |
| 2009/0222002 A1 | 9/2009 | Bonn et al. |
| 2009/0228003 A1* | 9/2009 | Sinelnikov ............ 606/41 |
| 2010/0114086 A1* | 5/2010 | Deem et al. ............ 606/33 |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 481 685 | 4/1992 |
| EP | 0 521 264 | 1/1993 |
| EP | 0 541 930 | 5/1993 |
| EP | 0 556 705 | 8/1993 |
| EP | 0 558 429 | 9/1993 |
| EP | 0 572 131 | 12/1993 |
| EP | 0 836 868 | 4/1998 |
| EP | 1 159 926 | 5/2001 |
| FR | 179607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |
| WO | 9904704 | 2/1999 |
| WO | 9922657 | 5/1999 |
| WO | WO 9953853 | 10/1999 |
| WO | 03039385 | 5/2003 |

OTHER PUBLICATIONS

U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/123,645, filed May 20, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/241,861, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
U.S. Appl. No. 12/242,102, filed Sep. 30, 2008.
U.S. Appl. No. 12/242,026, filed Sep. 30, 2008.

U.S. Appl. No. 12/242,061, filed Sep. 30, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/508,700, filed Jul. 24, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/556,238, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 29/341,411, filed Aug. 5, 2009.
U.S. Appl. No. 29/341,481, filed Jun. 8, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Cosman et al., "Methods of Making Nervous System Lesions" In William RH, Rengachary SS (eds): Neurosurgery, New York: McGraw•Hill, vol. 111, (1984), pp. 2490-2499.
Crawford et al., "Use of the LigaSure™ Vessel Sealing System in Urologic Cancer Surger" Grand Rounds in Urology 1999, vol. 1, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Heniford et al., "Initial Results with an Electrothermal Bipolar Vessel Sealer" Surgical Endoscopy (2001) 15:799-801.

Herman at al., "Laparoscopic Intestinal Resection With the LigaSure™ Vessel Sealing System: A Case Report" Innovations That Work, Feb. 2002.

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Johnson et al., "Evaluation of a Bipolar Electrothermal Vessel Sealing Device in Hemorrhoidectomy" Sales/Product Literature, Jan. 2004.

Jarrett et al., "Use of the LigaSure™ Vessel Sealing System for Peri-Hilar Vessels in Laparoscopic Nephrectomy" Sales/Product Literature 2000.

Johnson, "Evaluation of the LigaSure™ Vessel Sealing System in Hemorrhoidectormy" American College of Surgeons (ACS) Clinic La Congress Poster (2000).

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General, Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, pp. 205-210.

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTECH product literature (Mar. 2000) I'D Wire: product description, 1 page.

MDTECH product literature (Dec. 1999) "FlexStrand": product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157

"Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure™ Vessel Sealing System in Minimally Invasive Surgery in Children" Int'l Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques, vol. 44, No. 10, pp. 1832-1840, Oct. 1995.

T. Matsukawa et al., "Percutaneous Microwave Coagulation Therapy in Liver Tumors", Acta Radiologica, vol. 38, pp. 410-415, 1997.

T. Seki et al., (1994) "Ultrasonically Guided Percutaneous Microwave Coagulation Therapy for Small Hepatocellular Carcinoma," Cancer 74(3):817•825.

S. Humphries Jr. et al., "Finite•Element Codes to Model Electrical Heating and Non•LInear Thermal Transport in Biological Media", Proc. ASME HTD-355, 131 (1997).

Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.

Urrutia et al., (1988). "Retractable-Barb Needle for Breast Lesion Localization: Use in 60 Cases," Radiology 169(3):845-847.

Valleylab Brochure, "Valleylab Electroshield Monitoring System" 2 pages, Nov. 1995.

ValleyLab Brochure, "Electosurgery: A Historical Overview", Innovations in Electrosurgery, 1999.

Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report EP10010943 dated Feb. 1, 2011.
U.S. Appl. No. 08/483,742, filed Jun. 7, 1995.
U.S. Appl. No. 08/136,098, filed Oct. 14, 1993.

* cited by examiner

MICROWAVE SURFACE ABLATION USING CONICAL PROBE

BACKGROUND

1. Technical Field

The present disclosure relates to systems and methods for providing energy to biological tissue and, more particularly, to a microwave ablation surgical antenna having a conical aperture, and methods of use and manufacture therefor.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator. In tissue ablation electrosurgery, the radio frequency energy may be delivered to targeted tissue by an antenna or probe.

Presently, there are several types of microwave probes in use, e.g., monopole, dipole, and helical. One type is a monopole antenna probe, which consists of a single, elongated microwave conductor exposed at the end of the probe. The probe is typically surrounded by a dielectric sleeve. The second type of microwave probe commonly used is a dipole antenna, which consists of a coaxial construction having an inner conductor and an outer conductor with a dielectric junction separating a portion of the inner conductor. The inner conductor may be coupled to a portion corresponding to a first dipole radiating portion, and a portion of the outer conductor may be coupled to a second dipole radiating portion. The dipole radiating portions may be configured such that one radiating portion is located proximally of the dielectric junction, and the other portion is located distally of the dielectric junction. In the monopole and dipole antenna probe, microwave energy generally radiates perpendicularly from the axis of the conductor.

The typical microwave antenna has a long, thin inner conductor that extends along the axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

In the case of tissue ablation, a high radio frequency electrical current in the range of about 500 MHz to about 10 GHz is applied to a targeted tissue site to create an ablation volume, which may have a particular size and shape. Ablation volume is correlated to antenna design, antenna performance, antenna impedance and tissue impedance. The particular type of tissue ablation procedure may dictate a particular ablation volume in order to achieve a desired surgical outcome. By way of example, and without limitation, a spinal ablation procedure may call for a longer, more narrow ablation volume, whereas in a prostate ablation procedure, a more spherical ablation volume may be required. In some instances, targeted lesions may be located on or near the surface of the target organ. Such surface lesions have been treated with invasive ablation needles or sticks, which may cause damage to adjacent anatomical structures, increase the likelihood of hemorrhaging, and lengthen operative and recovery times.

SUMMARY

The present disclosure provides an electromagnetic surgical ablation probe having a distal conical aperture. The disclosed antenna includes a tubular catheter longitudinally disposed thereabout that is configured to circulate a coolant, such as saline or deionized water. At a distal end of the antenna, the catheter flares out distally to form a conical hood having a wide distal opening. The angle of flare may be dependent upon the desired radiating efficiency and radiating pattern at the intended frequency of operation. The conical hood may contain coolant delivered via the catheter and, additionally or alternatively, the conical hood may contain dielectric material. A membrane or plate constructed from radiofrequency-transparent material of low electrical conductance encloses the wide distal opening of the hood to form a tissue interface, e.g., a treatment surface. Any suitable radiofrequency-transparent material of low electrical conductance may be used, for example, high-temperature-resistant polymer or glass epoxy composite.

Radiofrequency energy is supplied to the antenna by a coaxial feedline having an inner conductor, an outer conductor disposed coaxially thereabout, and a dielectric disposed therebetween. The coaxial feedline passes longitudinally from a proximal end of the antenna, through the catheter, to a distal end of the antenna. A radiating section disposed within the conical hood is electrically coupled to the inner conductor. The radiating section may have a conical shape having a narrow proximal end coupled to the inner conductor, and a wide distal end extending toward the radiofrequency-transparent membrane or plate. The radiating section may additionally or alternatively include a flared section, a spiral section, and/or be loaded with disks, which may improve radiating performance and mechanical strength. Additionally or alternatively, the inner conductor may include a sharp tip that protrudes beyond the distal end of the conical opening, or may terminate within the cone. During use, the sharp tip may assist in positioning the antenna on tissue, and/or may improve radiation performance.

In one embodiment, the disclosed electromagnetic surgical ablation probe includes a coaxial feedline having an inner conductor, an outer conductor disposed coaxially thereabout, and a dielectric disposed therebetween. A tubular catheter is disposed coaxially around the feedline to form a fluid path. At a proximal end of the instrument the fluid path is in fluid communication with a source of coolant, which may be a coolant pump or gravity-assisted drip. A distal end of the fluid path is in fluid communication with a coolant chamber as will be described in detail hereinbelow. The disclosed probe includes an outer tube, e.g., a hypotube, that is coaxially disposed around the tubular catheter. A reflector, which may have a conical shape that includes a flared distal opening, is disposed at a distal end of the hypotube. A radiating section is disposed within the conical reflector, and is operably coupled to the inner conductor. The probe includes a membrane disposed across the distal opening of the conical reflector to define the coolant chamber. The reflector may additionally or alternatively have a hemispherical shape, trumpet-flared shape, frustoconical, or other flared shape.

The reflector may include at least one dielectric material. The dimensions of the dielectric material, e.g., thickness, shape, and/or position, may be determined by the desired characteristics of the probe, such as without limitation, impedance matching and ablation (radiation) pattern.

Also disclosed is an electromagnetic surgical ablation system that includes a source of microwave ablation energy operatively coupled to an electromagnetic ablation probe as disclosed herein. The source of microwave ablation energy may include a selectively activatable microwave generator configured to supply microwave or RF energy in a range of about 915 MHz to about 2450 MHz, or additionally or alternatively, microwave or RF energy in a range of about 500 MHz to about 10 GHz. A microwave generator in accordance with the present disclosure may include the capability to deliver ablation energy at a fixed-frequency and/or at a variable frequency. The microwave ablation probe may include a proximal handle portion and a distal shaft portion.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
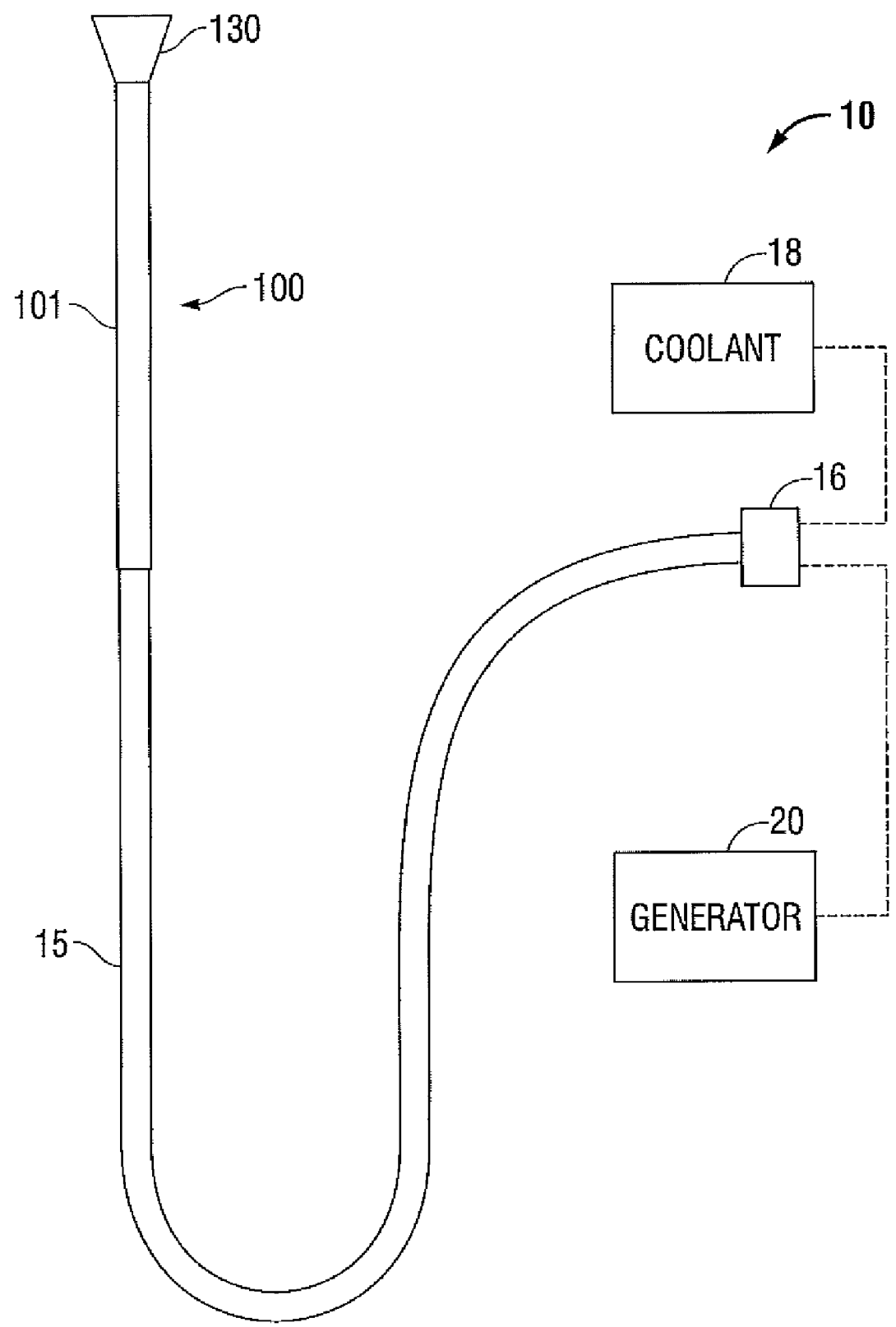
FIG. 1 shows a diagram of a microwave ablation system having an electromagnetic surgical ablation probe in accordance with the present disclosure.

Particular embodiments of the present disclosure will be described hereinbelow with reference to the accompanying drawings; however, it is to be understood that the disclosed embodiments are merely exemplary of the disclosure, which may be embodied in various forms. Well-known or repetitive functions, constructions are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to the user, while the term "distal" shall refer to the end that is farther from the user.

FIG. 1 shows an embodiment of a microwave ablation system 10 in accordance with the present disclosure. The microwave ablation system 10 includes a electromagnetic surgical ablation probe 100 connected by a cable 15 to connector 16, which may further operably connect the antenna probe 100 to a generator assembly 20. Generator assembly may be a source of ablation energy, e.g., microwave or RF energy in the range of about 915 MHz to about 2450 MHz. Cable 15 may additionally or alternatively provide a conduit (not explicitly shown) configured to provide coolant from a coolant source 18 to the electromagnetic surgical ablation probe 100.

Figure 2:
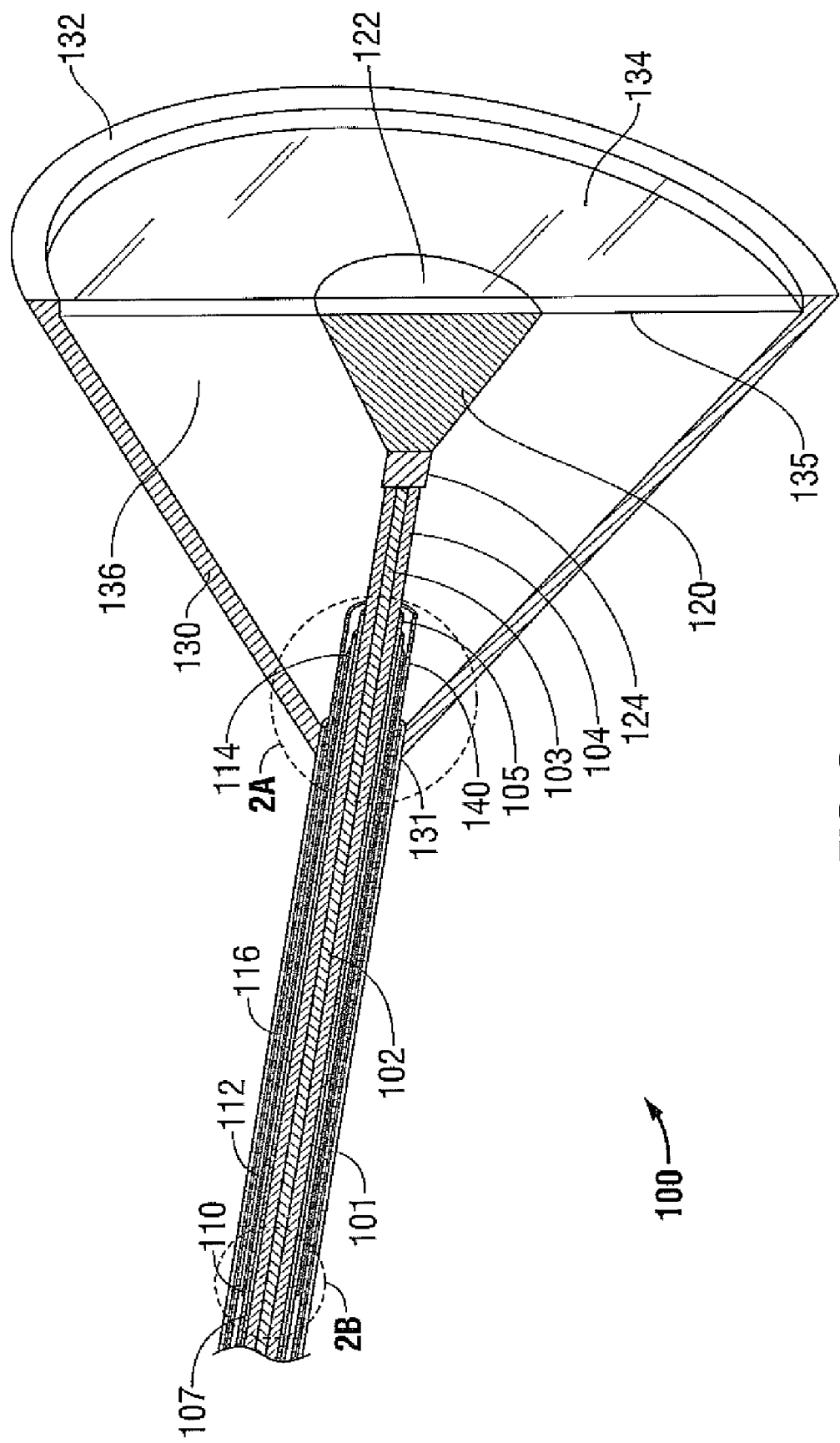
FIG. 2 shows a cross sectional perspective view of an embodiment of an electromagnetic surgical ablation probe in accordance with the present disclosure.

In greater detail, FIG. 2 shows an embodiment of an electromagnetic surgical ablation probe 100 having a shaft assembly 101 and a conical hood 130 disposed at the distal end of the shaft 101. The conical hood 130 is arranged having an apex end 131 (e.g., narrow end) thereof oriented proximally and an open base end 132 (e.g., wide end or mouth) oriented distally.

Figure 2A:
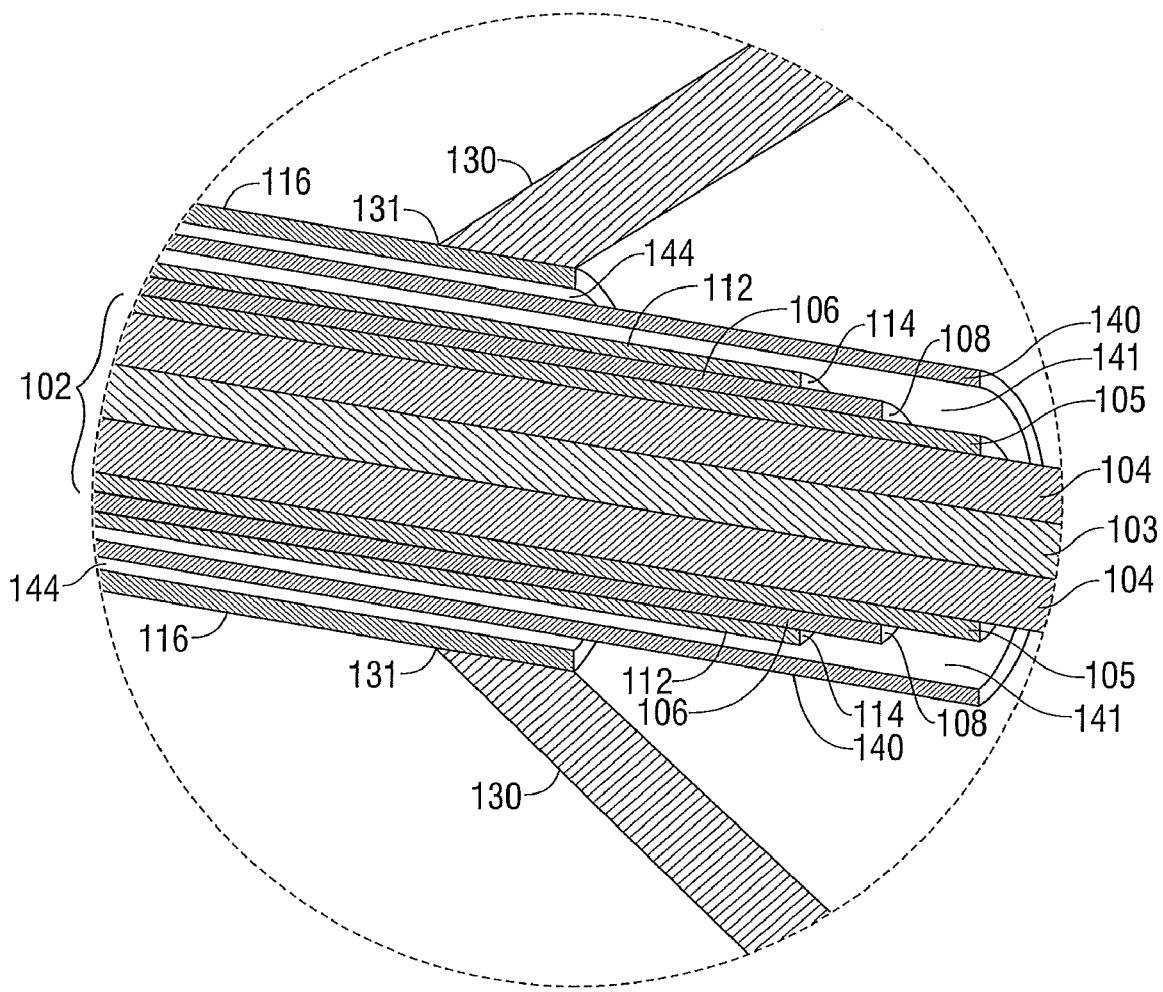
FIG. 2A shows a detail view of a distal section of an embodiment of an electromagnetic surgical ablation probe in accordance with the present disclosure.
Figure 2B:
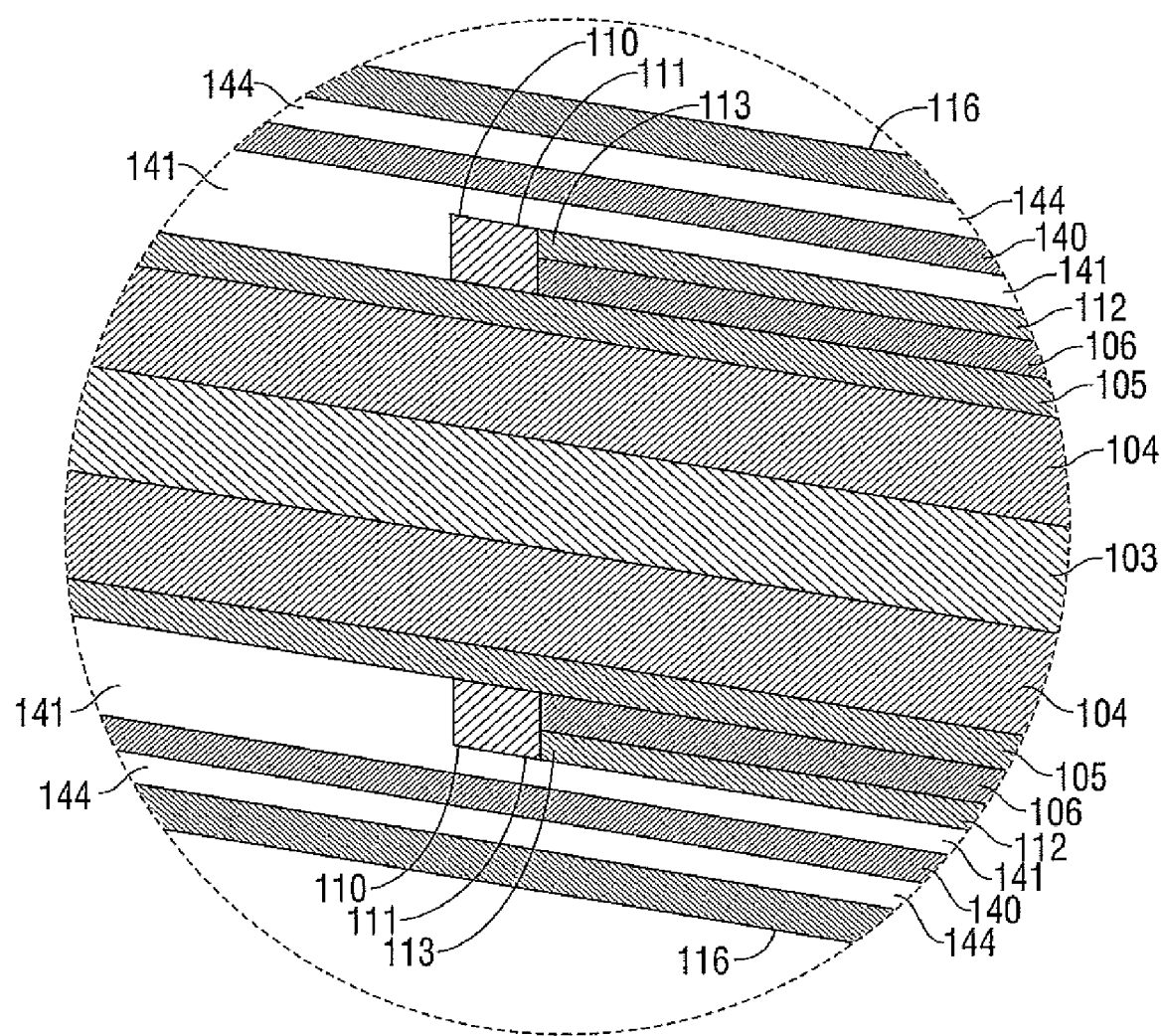
FIG. 2B shows a detail view of a proximal section of an embodiment of an electromagnetic surgical ablation probe in accordance with the present disclosure.

As seen in FIGS. 2A and 2B, the shaft assembly 101 includes a coaxial feedline 102 having an inner conductor 103, a dielectric 104 coaxially disposed about the inner conductor 103, and an outer conductor 105 coaxially disposed about the dielectric 104. At a distal end of the feedline 102 the inner conductor 103 and dielectric 104 extend beyond the outer conductor 105. A distal radiating section cylinder 124 is coupled to a distal end of the inner conductor 103. A distal radiating section cone 120 is coupled at a proximal end 121 thereof to a distal end 125 of distal radiating section cylinder 124. In an embodiment, distal radiating section cylinder 124 and distal radiating section cone 120 may be integrally formed. Inner conductor 103, distal radiating section cylinder 124, and distal radiating section cone 120 may be coupled by any suitable manner of bonding, including without limitation welding, soldering, crimping, or threaded fastening.

A proximal end of feedline 102 may be operably coupled to a source of microwave ablation energy in the range of about 915 MHz to about 5 GHz.

Figure 6A:
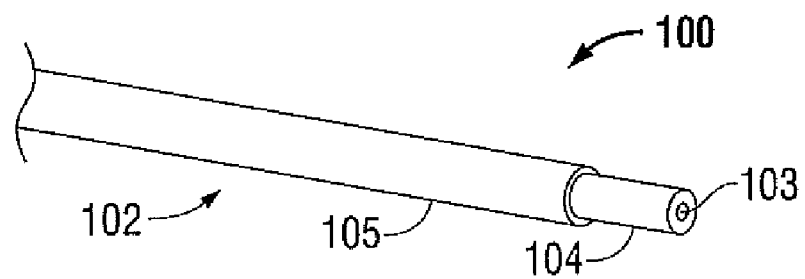
FIGS. 6A-6J show views of an embodiment of an electromagnetic surgical ablation probe at various stages of manufacture.
Figure 6B:
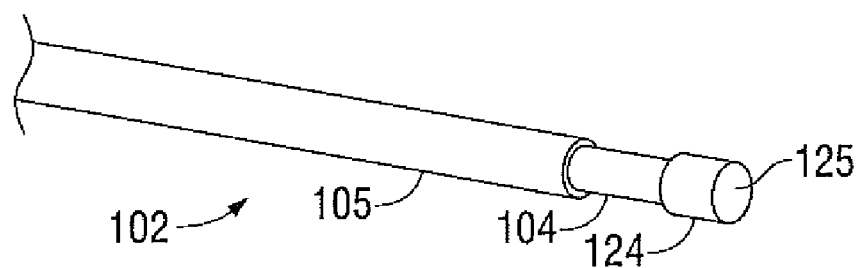
Figure 6C:
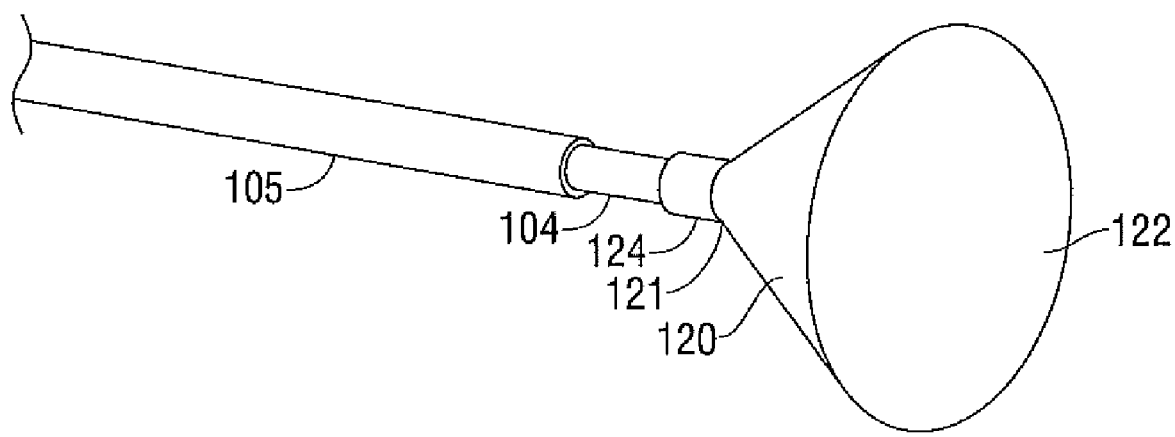
Figure 6D:
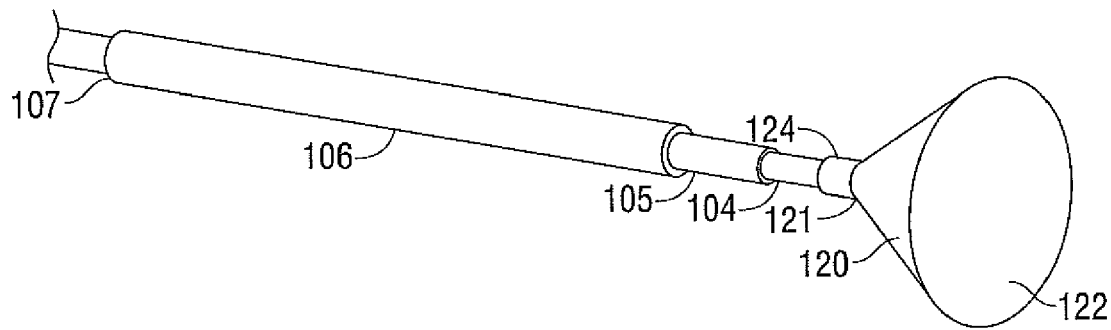
Figure 6E:
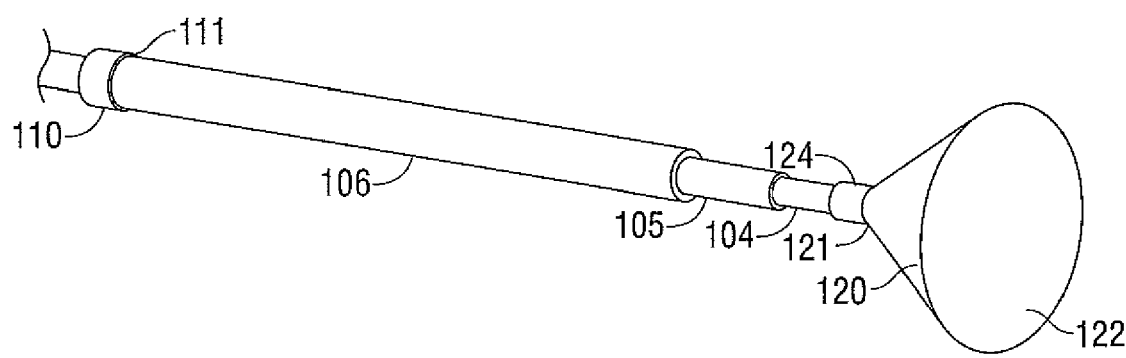
Figure 6F:
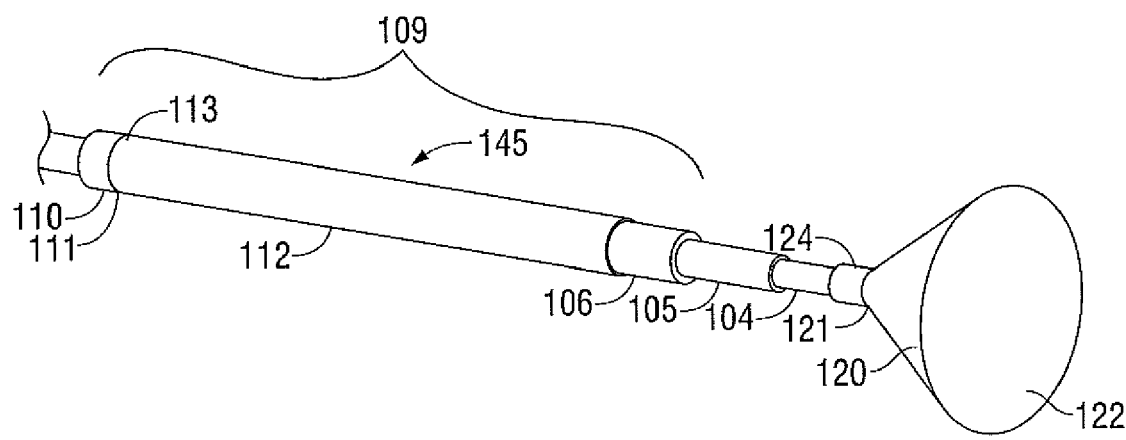

As seen in FIG. 6F, a balun 109 that includes balun short 110, balun outer conductor 112, and balun insulator 106 provides a high-impedance RF path which may define an ablation pattern, e.g., may confine or focus an ablation pattern to a distal end of the probe. Balun 109 may prevent RF energy from propagating distally along, e.g., inflow fluid path 141 or outflow fluid path 144. Balun short 110 is disposed coaxially around and electrically coupled to outer conductor 105 of feedline 102. Balun outer conductor 112 is coaxially disposed about feedline 102 and insulated therefrom along the length of balun outer conductor 112 by balun insulator 106. Balun insulator 106 is coaxially disposed between balun outer conductor 112 and outer conductor 105. Balun short 110 and balun outer conductor 112 may be electrically coupled. Balun short 110 has a generally ring-like or truncated tubular shape and is disposed at a proximal end 107 of balun insulator 106.

Balun outer conductor 112 has a substantially tubular shape, having a proximal end 113 thereof abutting a distal end 111 of balun short 110 and extending distally. A distal end 114 of balun outer conductor 112 is positioned substantially adjacent to a distal end 108 of balun insulator 106. Balun insulator 106 may extend distally beyond a distal end 114 of balun outer conductor 112 to enhance microwave performance of the probe, e.g., provide a desired ablation pattern.

A divider tube 140 is concentrically disposed between a hypotube 116 and the inner components of the shaft assembly 101, e.g., feedline 102 and/or balun 109 components, to define a fluid outflow path 144 between hypotube 116 and divider tube 140, and a fluid inflow path 141 between divider tube 140 and feedline 102 and/or balun 109. At a proximal end thereof, fluid inflow path 141 may be in fluid communication with a source of coolant, such as saline or deionized water. At a distal end thereof, fluid inflow path 141 and fluid outflow path 144 are in fluid communication with an interior volume of conical hood 130. A distal end of divider tube 140 may protrude distally beyond a distal end of hypotube 116. Hypotube 116 may be formed from any sufficiently strong electrically-conductive heat-resistant material, e.g., stainless steel. A proximal apex end 131 of conical hood 130 may include an opening (not explicitly shown) that is dimensioned to engage a distal end of hypotube 116. Conical hood 130 may be coupled to hypotube 116 by any suitable manner of bonding, such as welding, soldering, crimping, adhesive, or by integral forming.

A membrane 134 is disposed across the perimeter of distal opening 132 of conical hood 130 to define a fluid chamber 136. Membrane 134 may be formed of any suitable radiofrequency-transparent material of low electrical conductivity, e.g., material that enables efficient transmissivity of microwave ablation signals to tissue from the energy delivery system, including without limitation, the conical radiating structure herein described. Membrane 134 may be formed from a rigid material, or may be formed from flexible and/or elastomeric material. Membrane 134 is sealed to distal opening 132 by any manner of coupling that is resistant to the passage of fluid. The distal surface 122 of distal radiating section cone 120 may be positioned in a coplanar arrangement with proximal surface 135 of membrane 134.

In use, coolant, e.g., saline or deionized water (not explicitly shown) flows distally through fluid inflow path 141, into fluid chamber 136, and proximally through fluid outflow path 144. Fluid chamber 136 may become filled with coolant. The circulation of coolant in this manner may aid in controlling ablation temperature of tissue, ablation patterns, and/or may improve impedance matching due to, at least in part, the dielectric properties of the coolant. In embodiments, the relative positions of fluid inflow path 141 and fluid outflow path 144 may differ from that described hereinabove, e.g., reversed (fluid inflow path 141 may be defined coaxially around fluid outflow path 144), or defined by one or more longitudinal ribs, without departing from the spirit and scope of the present disclosure.

Figure 3:
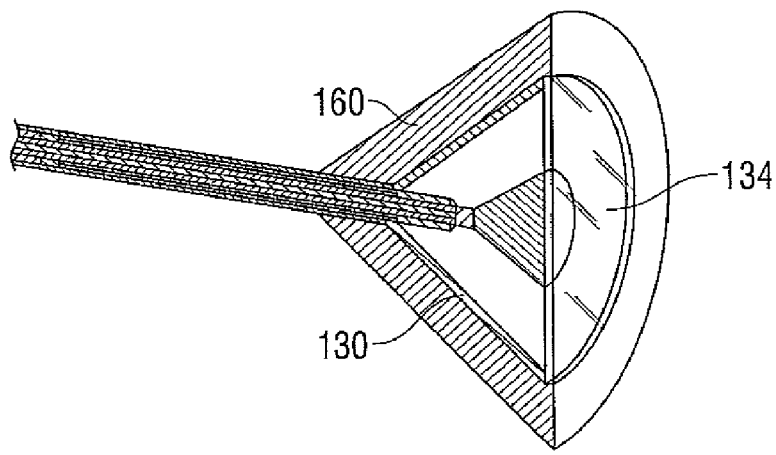
FIG. 3 shows a cross sectional perspective view of another embodiment of an electromagnetic surgical ablation probe in accordance with the present disclosure.

In an embodiment best represented in FIG. 3, a dielectric layer 160 may be disposed on a surface of conical hood 130, and, additionally or alternatively, around an adjacent length of hypotube 116, which may additionally aid in impedance matching and ablation pattern control. Additionally or alternatively, dielectric layer 160 may include multiple layers and/or multiple sections arranged to direct and/or absorb microwave energy to form specific ablation patterns (not explicitly shown). Microwave ablation energy is conducted by feedline 102 from a source of microwave ablation energy (not explicitly shown) to distal radiating section cone 120 for delivery to tissue.

Figure 4:
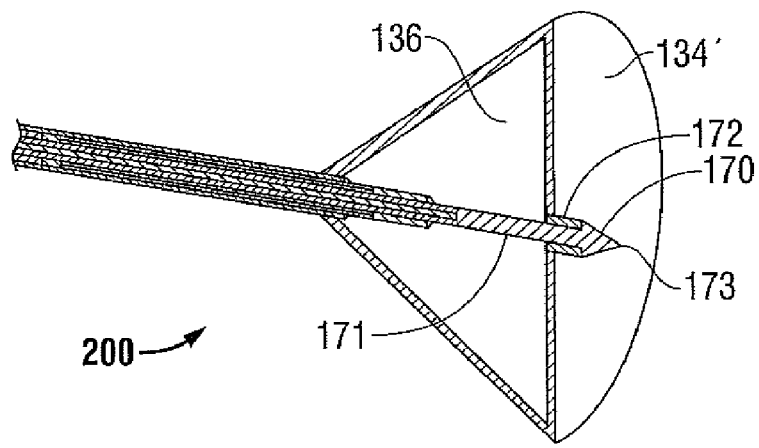
FIG. 4 shows a cross sectional perspective view of yet another embodiment of an electromagnetic surgical ablation probe in accordance with the present disclosure.

Turning now to FIG. 4, an embodiment of a microwave ablation probe 200 in accordance with the present disclosure includes distal radiating tip 170 which protrudes through a corresponding aperture (not explicitly shown) provided by membrane 134'. Tip 170 has conical shape having a distally-facing apex 173 (e.g., a point) that is adapted to contact tissue. A distal radiating section cylinder 171 extends from a distal end of the feedline 102 to the proximal base of tip 170. A seal 172 is provided that is adapted to contain coolant within a coolant chamber 136. Seal 172 may be formed from any suitable heat-resistant material, including without limitation heat-resistant elastomeric material. Tip 170 may be coated with a non-stick material, such as polytetrafluoroethylene (a.k.a. PTFE or Teflon®, manufactured by the E.I. du Pont de Nemours and Co, of Wilmington, Del., USA), polyethylene tephthalate (PET), or the like.

Figure 5:
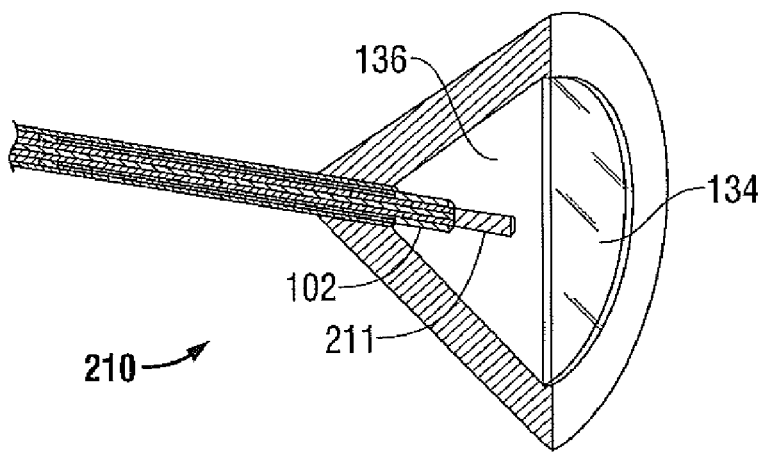
FIG. 5 shows a cross sectional perspective view of still another embodiment of an electromagnetic surgical ablation probe in accordance with the present disclosure.

In yet another embodiment according to the present disclosure and depicted in FIG. 5, a microwave ablation probe 210 includes a distal radiating section 211 having a substantially rod-like or elongate cylindrical shape. The distal radiating section cylinder 211 extends from a distal end of the feedline 102 to an interior portion of coolant chamber 136. A proximal end of distal radiating section 211 is operably coupled to inner conductor 103 of feedline 102.

Figure 8A:
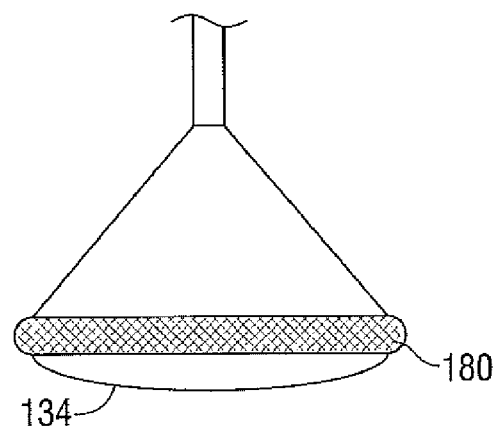
FIGS. 8A-8C show aspects of the FIG. 7 embodiment of an electromagnetic surgical ablation probe in use.
Figure 8B:
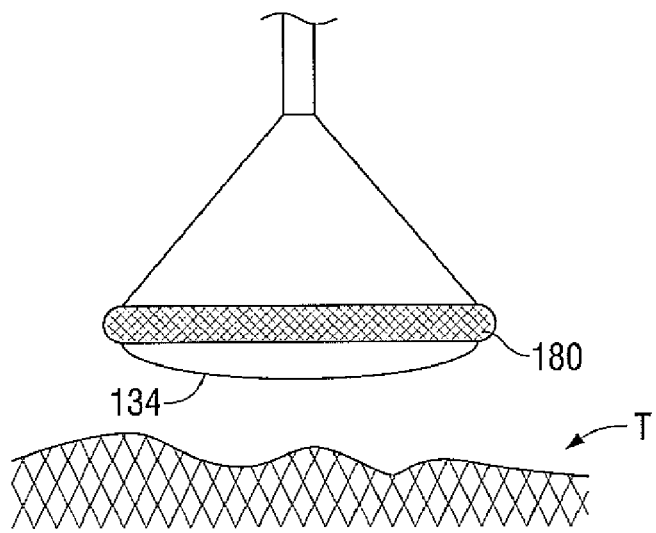
Figure 8C:
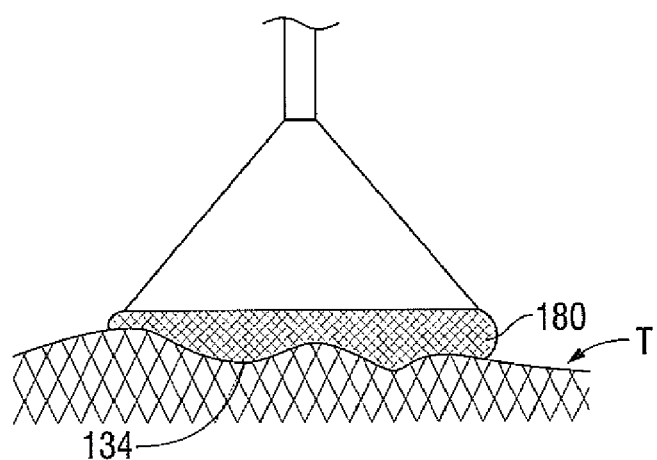

Still another embodiment in accordance with the present disclosure is presented in FIGS. 7, 8A, 8B, and 8C, wherein a microwave ablation probe 220 includes a conformable aperture 180 disposed about the perimeter of distal opening 132 of conical hood 130. Conformable aperture 180 may be constructed of any suitable material, including without limitation, elastomeric material, woven material, mesh material, conductive material, and dielectric material. In an embodiment, conformable aperture 180 is formed from stainless steel mesh. As best shown in FIGS. 8A, 8B, and 8C, the compliant properties of conformable aperture 180 and, additionally or alternatively, membrane 134, may enable the same to achieve improved contact with tissue T during an ablation procedure. In use, coolant pressure may be adjusted to deform membrane 134 inwardly or outwardly to achieve the desired contact between membrane 134, conformable aperture 180 and tissue T.

Figure 9A:
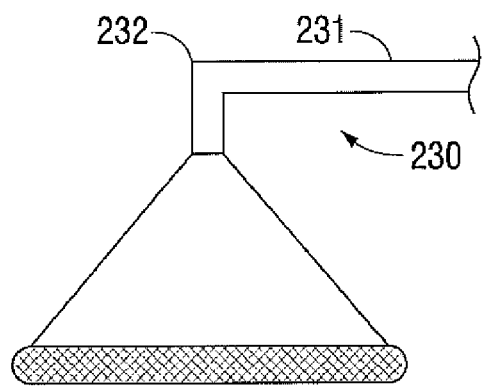
FIGS. 9A-9C illustrate embodiments of an electromagnetic surgical ablation probe having an alternate shaft arrangements in accordance with the present disclosure.
Figure 9B:
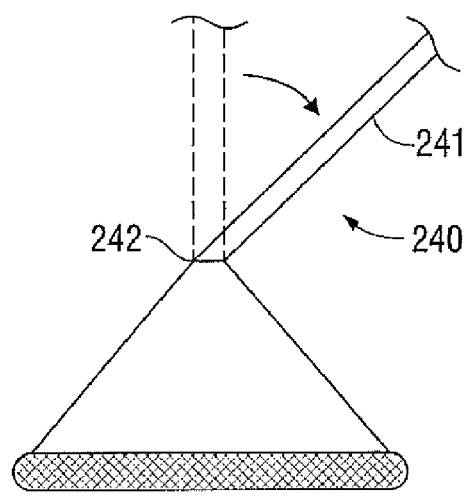
Figure 9C:
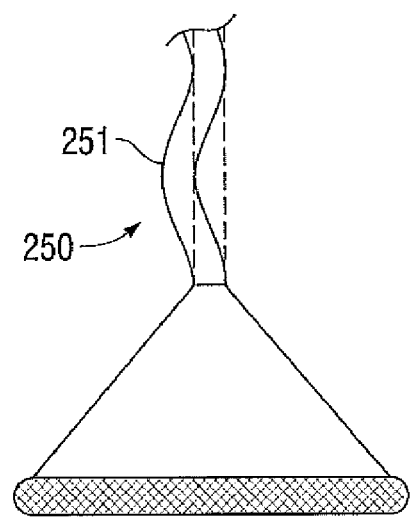

Turning now to FIGS. 9A, 9B, and 9C, embodiments in accordance with the present disclosure are presented wherein a microwave ablation probe 230 includes a shaft having a bent or angled section. For example without limitation, and as best shown in FIG. 9A, a shaft 231 may include a pre-formed bend 232 having an angle of about 90°. In other envisioned embodiments (not explicitly shown), bend 232 may describe any pre-formed angle, such as about 30°, about 45°, or about 75°. In FIG. 9B, a microwave ablation probe 240 includes an adjustable joint 242 between a distal end of shaft 241 and conical hood 130 that is configured to facilitate adjustment of the angle of shaft 241 relative to conical hood 130. In one envisioned embodiment, joint 242 includes a ball and socket arrangement having sufficient friction, or preload, therebetween to enable a surgeon to set the shaft angle as desired by overcoming the frictional preload to position the shaft 241 to a desired angle, whereafter the frictional preload maintains the set angle. In yet another embodiment, the angle between a shaft 241 and hood 130 may be changed by manipulating an actuator (not explicitly shown) on, for example, a proximal end of shaft 241 or a housing (not explicitly shown) operable coupled thereto.

In FIG. 9C another embodiment in accordance with the present disclosure is presented wherein a microwave ablation probe 250 includes a malleable shaft 251 that is formed at least in part from malleable material, such as without limitation, aluminum. In use, a surgeon may form the malleable shaft 251 into a desired shape by manual manipulation of the malleable shaft. A template (not explicitly shown) may be provided to assist in bending the shaft into a desired profile.

A method of manufacturing a microwave ablation probe 100 having a conical hood 130 is shown in accordance with the present disclosure with reference now to FIGS. 6A-6J. It is to be understood that the steps of the method provided herein may be performed in combination and in a different order than presented herein without departing from the scope and spirit of the present disclosure.

As shown in FIG. 6A, a coaxial feedline 102 is provided having an inner conductor 103, a dielectric 104 and an outer conductor 105. At a distal end thereof the inner conductor 103 and dielectric 104 extends beyond outer conductor 105. In one embodiment of the disclosed method, a stripping tool may be used to trim a distal portion of outer conductor 105 to expose inner conductor 103 and dielectric 104.

With reference to FIG. 6B, a distal radiating section cylinder 124 is provided and affixed to inner conductor 103 by any suitable manner of attachment, for example and without limitation, by laser welding. As shown in FIG. 6C, a radiating cone 120 is provided, having a generally conical shape and including a truncation at a proximal apex end 121 that is dimensioned to couple to a distal surface 125 of distal radiating section cylinder 124. Radiating cone 120 is affixed to distal radiating section cylinder 124 by any suitable manner of bonding, such as without limitation, by laser welding of threaded fastener.

Referring now to FIG. 6D, a balun insulator 106 is applied to coaxial feedline 102. Balun insulator 106 may be applied by any suitable manner, such as without limitation by applying a polymeric coating, and/or by positioning a heat-shrinkable tube (e.g., polyolefin) and raising the temperature thereof to conform the heat shrink tubing to the coaxial feedline 102. A balun short 110 is electrically coupled to outer conductor 105 of feedline 102 by any suitable manner of electrical connection, e.g., soldering, welding, or laser welding. A balun outer conductor 112 may be positioned over the balun insulator 106 as seen in FIGS. 6E and 6F to form a probe core assembly 145.

Figure 6G:
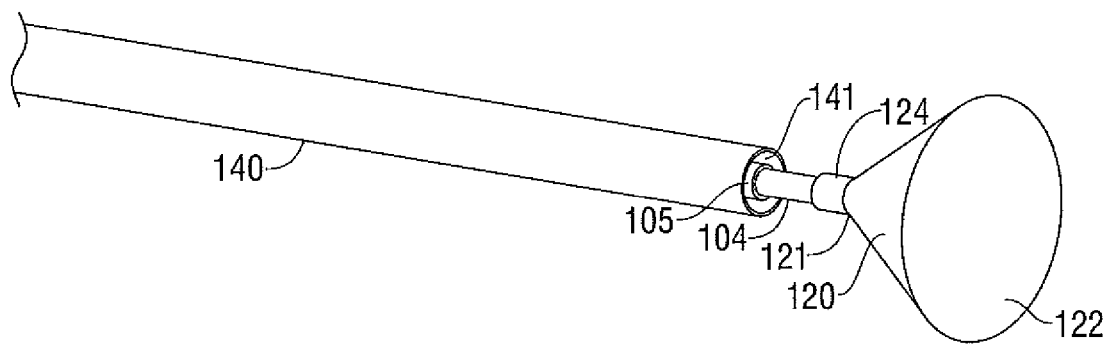
Figure 6H:
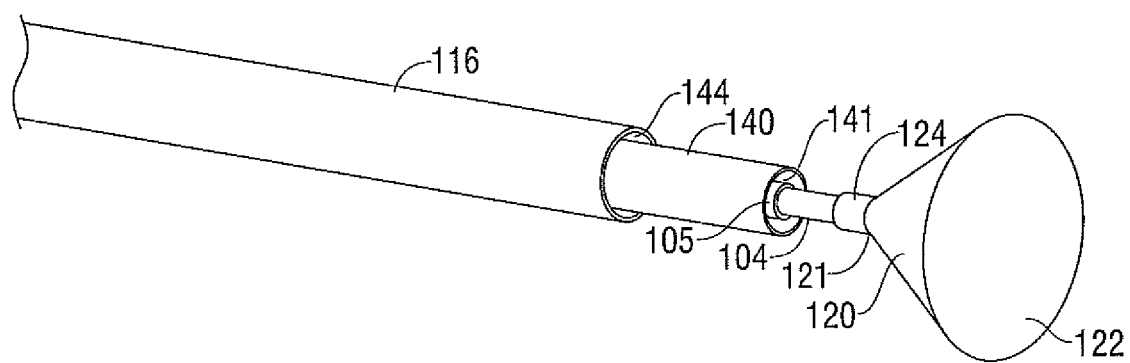
Figure 6I:
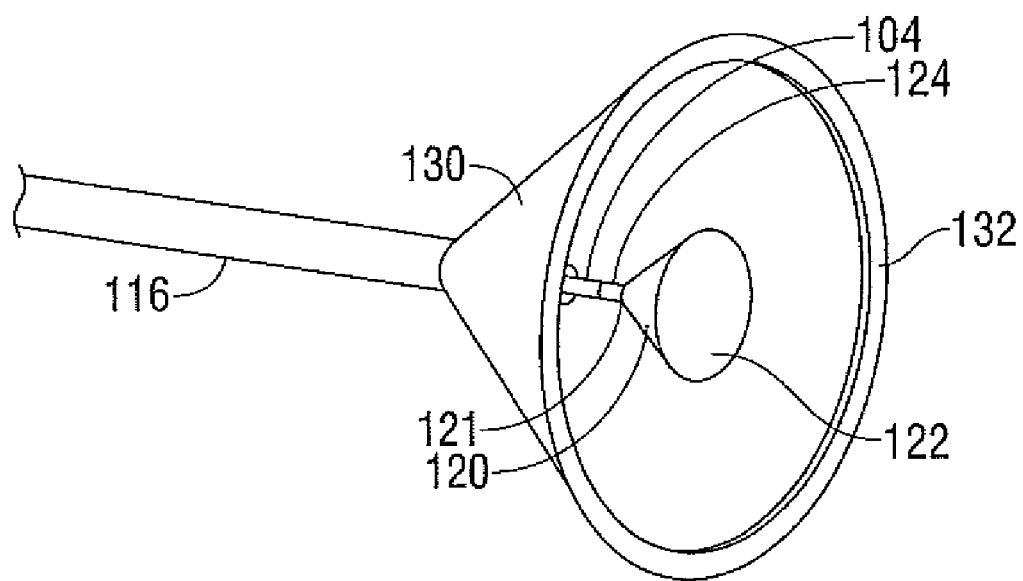

Turning now to FIG. 6G, a concentric divider tube 140 is positioned over probe core assembly 145. In an embodiment, at least one support is disposed between a surface of divider tube 140 and a surface of probe core assembly 145 and adapted to facilitate the flow of coolant through divider tube 140. As seen in FIG. 6H, a hypotube 116 is positioned over concentric divider tube 140. Conical reflector 130 is positioned in axial alignment with hypotube 116, such that a proximal opening disposed in a proximal apex end of conical reflector 130 is positioned substantially around a distal end of hypotube 116 as shown in FIG. 6I, forming a junction therebetween. Conical reflector 130 is affixed to hypotube 116 at said junction by any suitable manner of attachment, including laser welding. In an alternative embodiment, hypotube 116 and conical reflector 130 are integrally formed by, for example without limitation, cold rolling, forging, and/or die casting.

Figure 6J:
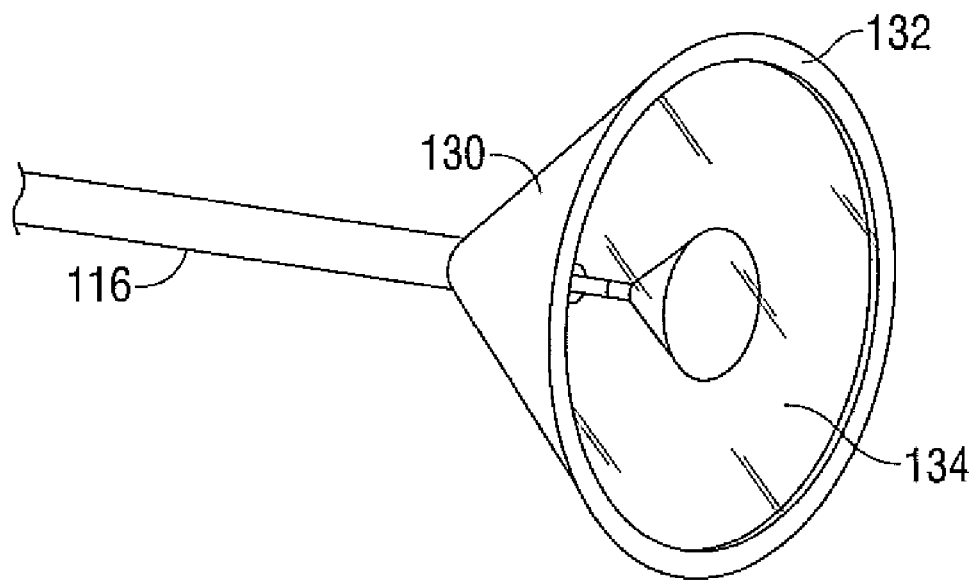
Figure 7:
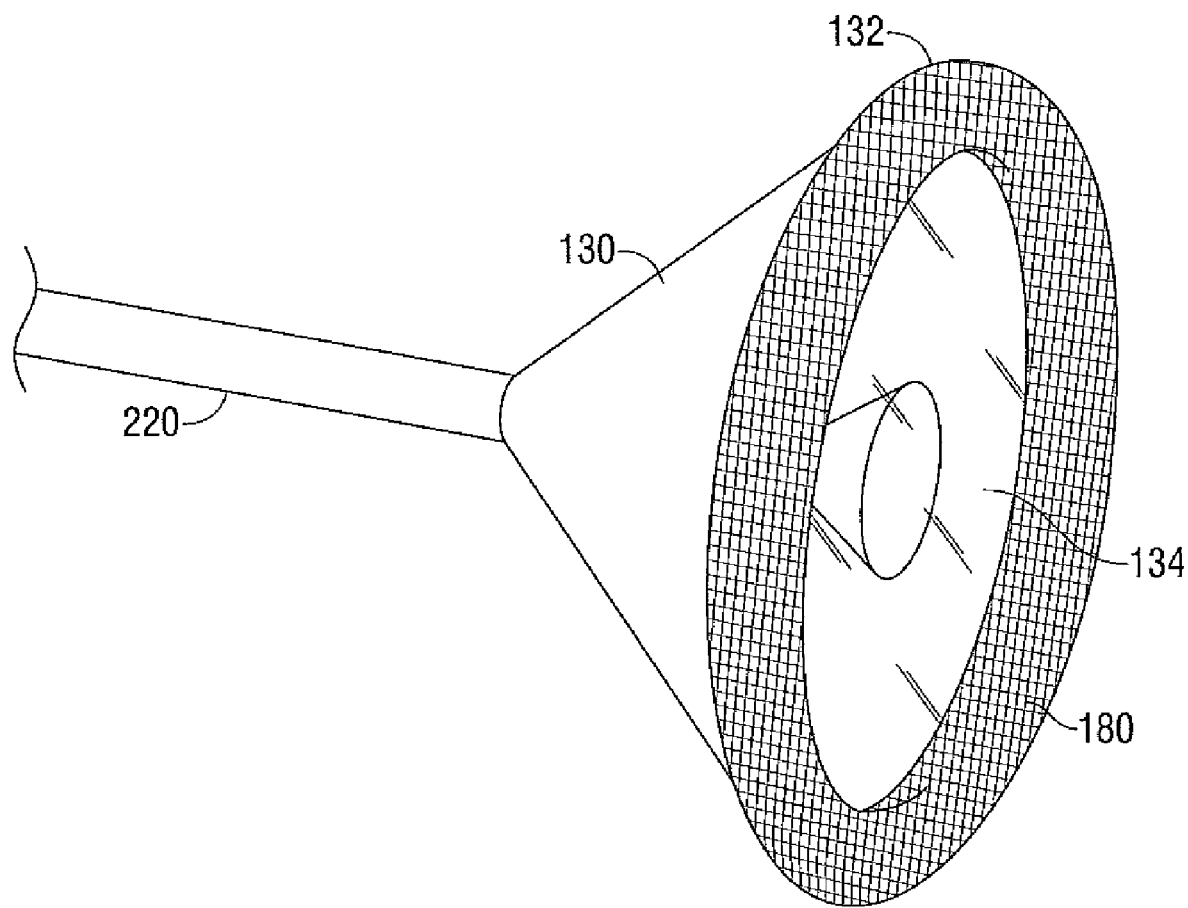
FIG. 7 shows a cross sectional perspective view of embodiment of an electromagnetic surgical ablation probe having a conformable mesh in accordance with the present disclosure.

With reference to FIG. 6J, a membrane 134 may be affixed to the perimeter of a distal opening 132 of conical reflector 130 by any suitable manner of attachment, for example, and without limitation, by adhesive, by rolled crimp, and/or by heat welding. In one embodiment, sheet stock or membrane 134 material is first placed under tension (e.g., stretched lengthwise and widthwise), affixed to a perimeter of distal opening 132 while under tension, and trimmed around the perimeter of distal opening 132 to form membrane 134 in situ. A conformable aperture 180 may be affixed to the perimeter of the distal base opening of the conical reflector.

Figure 10:
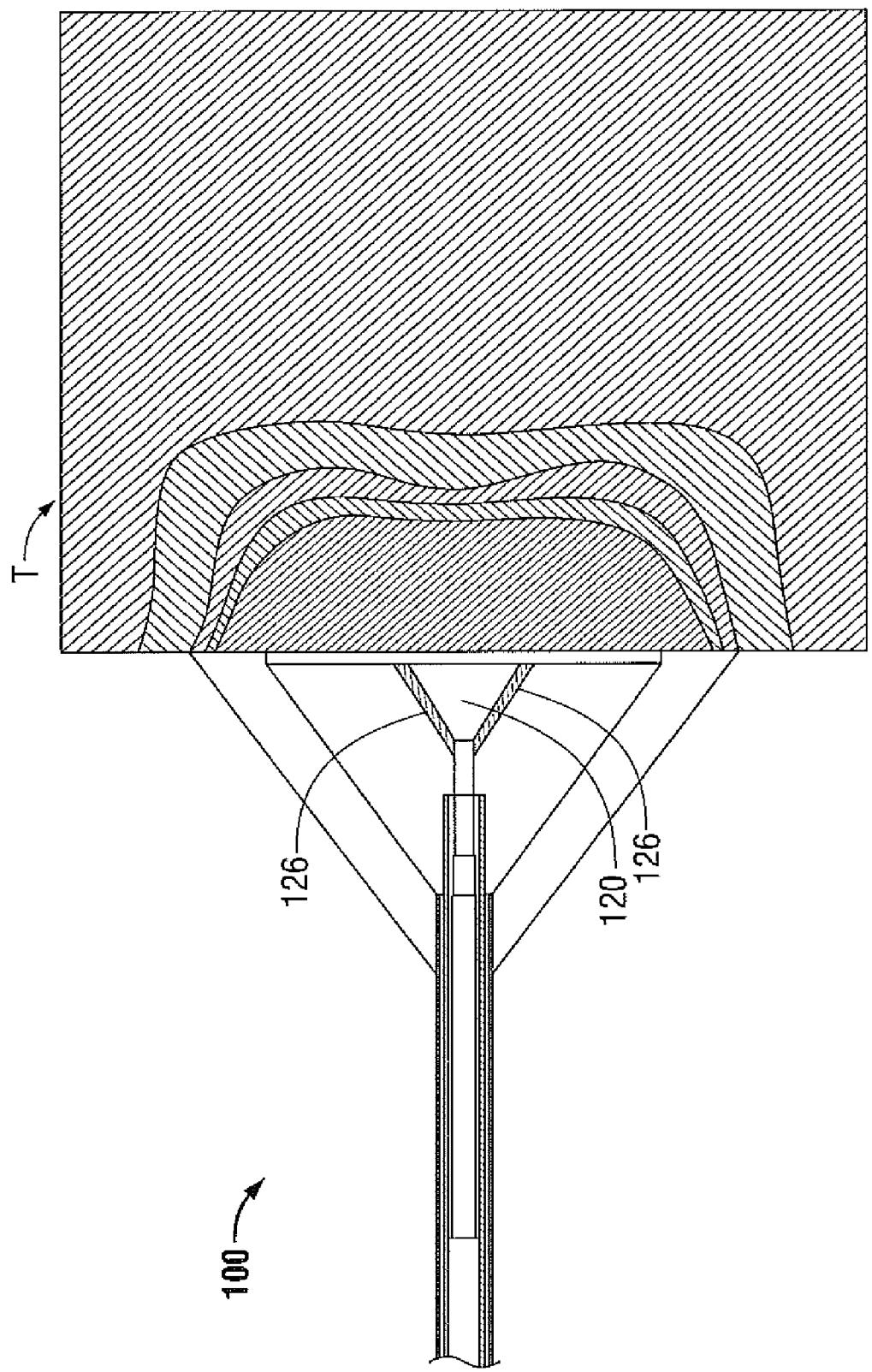
FIG. 10A illustrates penetration of electromagnetic energy into tissue of an embodiment of an electromagnetic surgical ablation probe in accordance with the present disclosure.
Figure 11A:
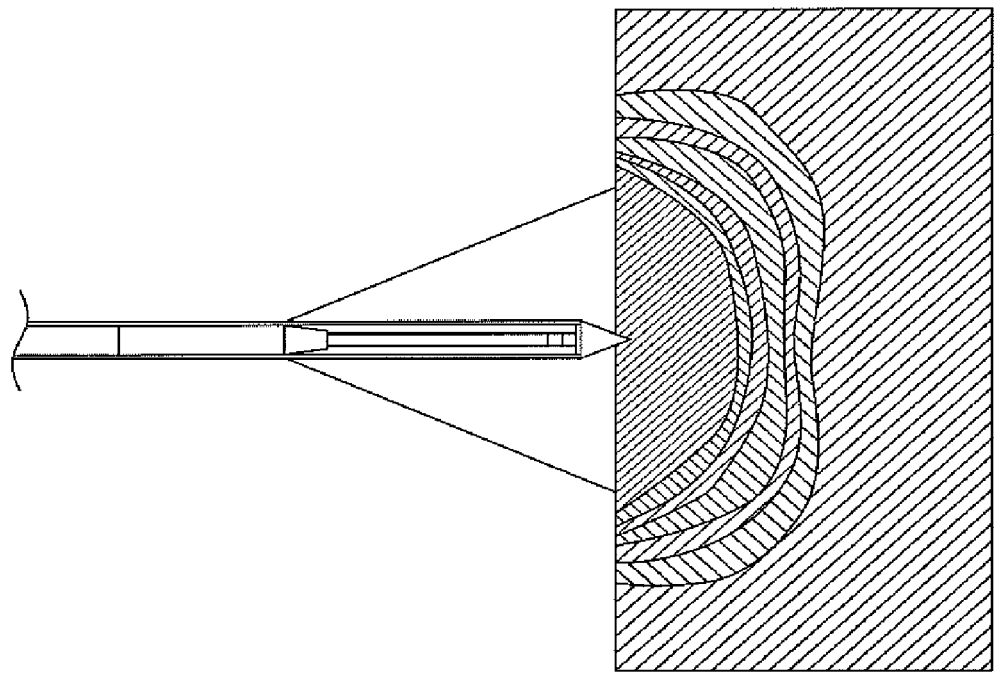
FIG. 11A illustrates penetration of electromagnetic energy into tissue of another embodiment of an electromagnetic surgical ablation probe in accordance with the present disclosure during an initial application of ablation energy.
Figure 11B:
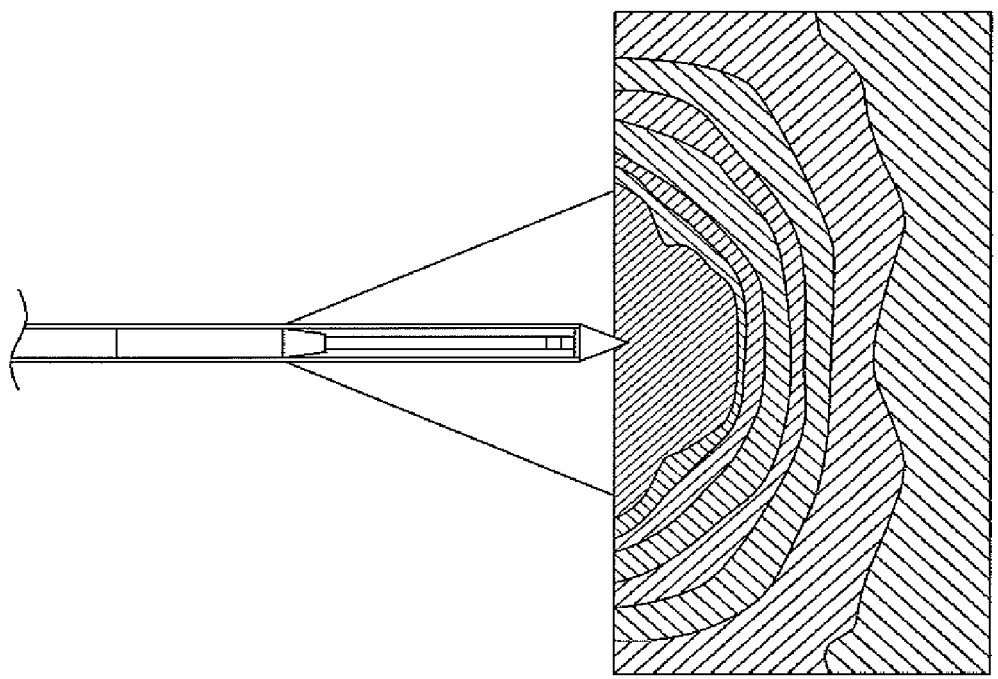
FIG. 11B illustrates penetration of electromagnetic energy into tissue of the FIG. 11A embodiment of an electromagnetic surgical ablation probe upon completion of an application of ablation energy.

A specific absorption rate (SAR) is a unit of measure proportional to the initial rate of temperature increase at a probe-tissue interface, and may be used to evaluate the amount and shape of energy (e.g., an ablation pattern) produced by a probe. FIG. 10 depicts a SAR pattern of a microwave ablation probe in accordance with the present disclosure. A dielectric layer 126 may be included on radiating cone 120, which may improve impedance matching between the instrument and tissue. FIGS. 11A and 11B shows a SAR pattern of another embodiment of the disclosed probe at the beginning and end of an ablation procedure, respectively.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. An electromagnetic surgical ablation probe, comprising:
    a coaxial feedline having an inner conductor, an outer conductor disposed coaxially thereabout, and a dielectric disposed therebetween;
    a tubular catheter coaxially disposed around the coaxial feedline configured to circulate a coolant to a coolant chamber;
    a hypotube coaxially disposed around the tubular catheter having a flared opening at a distal end thereof;
    a radiating section disposed within the flared opening and operably coupled to the inner conductor;

a membrane enclosing the flared opening to define the coolant chamber; and a conformable mesh disposed on a periphery of the flared opening.

2. The electromagnetic surgical ablation probe of claim 1, wherein the conformable mesh is formed from stainless steel.

3. An electromagnetic surgical ablation system, comprising:

a source of microwave ablation energy;

a coaxial feedline operatively coupled to the source of microwave ablation energy, wherein the coaxial feedline includes an inner conductor, an outer conductor disposed coaxially thereabout, and a dielectric disposed therebetween;

a tubular catheter coaxially disposed around the coaxial feedline, wherein the tubular catheter is configured to circulate a coolant to a coolant chamber;

a hypotube coaxially disposed around the tubular catheter having a flared opening at a distal end thereof;

a radiating section disposed within the flared opening and operably coupled to the inner conductor;

a membrane enclosing the flared opening to define the coolant chamber; and a conformable mesh disposed on a periphery of the flared opening.

* * * * *